US00PP21266P2

(12) United States Plant Patent
Jewell

(10) Patent No.: US PP21,266 P2
(45) Date of Patent: Aug. 31, 2010

(54) ***ASTELIA* PLANT NAMED 'ASTJEL01'**

(50) Latin Name: *Astelia chathamica*
Varietal Denomination: AstJel01

(76) Inventor: Geoff Jewell, Settlement RD 2, Otaki (NZ) 5582

( * ) Notice: Subject to any disclaimer, the term of this patent is extended or adjusted under 35 U.S.C. 154(b) by 0 days.

(21) Appl. No.: 12/383,760

(22) Filed: Mar. 27, 2009

(51) Int. Cl.
*A01H 5/00* (2006.01)

(52) U.S. Cl. ..... Plt./373

(58) Field of Classification Search ..... Plt./373
See application file for complete search history.

*Primary Examiner*—June Hwu

(57) ABSTRACT

A new and distinct *Astelia chathamica* cultivar named 'AstJe101' is disclosed, characterized by having distinctive dark bronze coloration of foliage, rapid early growth rate, slowing to a moderate, controlled growth rate. The new variety is an *Astelia chathamica*, normally produced as an outdoor garden or container plant.

2 Drawing Sheets

Latin name of the genus and species: *Astelia chathamica.*

Variety denomination: 'AstJe101'.

BACKGROUND OF THE INVENTION

The new cultivar was discovered as a result of a planned breeding program, conducted by the inventor, Geoff Jewell. *Astelia chathamica* plants were self-crossed, seeds collected and planted out during 1997 through 1999. The new variety was discovered, by the inventor in a planting of the resulting seedlings, in early 2001, at a commercial nursery in Te Horo, New Zealand.

Asexual reproduction of the new cultivar 'AstJe101' by division was first performed at a commercial nursery in late 2001, in Te Horo, New Zealand in and has shown that the unique features of this cultivar are stable and reproduced true to type on successive generations.

SUMMARY OF THE INVENTION

The cultivar 'AstJe101' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AstJe101' These characteristics in combination distinguish 'AstJe101' as a new and distinct *Astelia* cultivar:

1. Distinctive dark bronze coloration of foliage, darkness enhanced by cool temperatures.
2. Rapid early growth rate, growing quickly to fill a commercial 2.5 liter pot, then slowing to a moderate, controlled growth rate.

PARENT COMPARISON

Plants of the new cultivar 'AstJe101' are similar to plants of the parent variety, *Astelia chathamica* in most horticultural characteristics, however, plants of the new cultivar 'AstJe101' have darker foliage, with bronze coloration, compared to the species green foliage. Additionally, 'AstJe101' produces an overall shorter plant than the parent variety.

COMMERCIAL COMPARISON

Plants of the new cultivar 'AstJe101' are similar to plants of the unpatented variety, *Astelia chathamica* 'Silver Spear' in most horticultural characteristics, however, plants of the new cultivar 'AstJe101' have darker foliage, with bronze coloration, compared to the grey-green foliage of *Astelia chathamica* 'Silver Spear.' Additionally, 'AstJe101' produces an overall shorter plant than *Astelia chathamica* 'Silver Spear'.

BRIEF DESCRIPTION OF THE PHOTOGRAPH

The accompanying photograph in FIG. 1 illustrates in full color a typical plant of 'AstJe101' grown outdoors at a commercial nursery in Te Horo, New Zealand during late Winter and early Spring, in a 2.5 liter nursery pot. Age of the plant photographed is approximately 6 months from a vegetative division.

Figure 1:
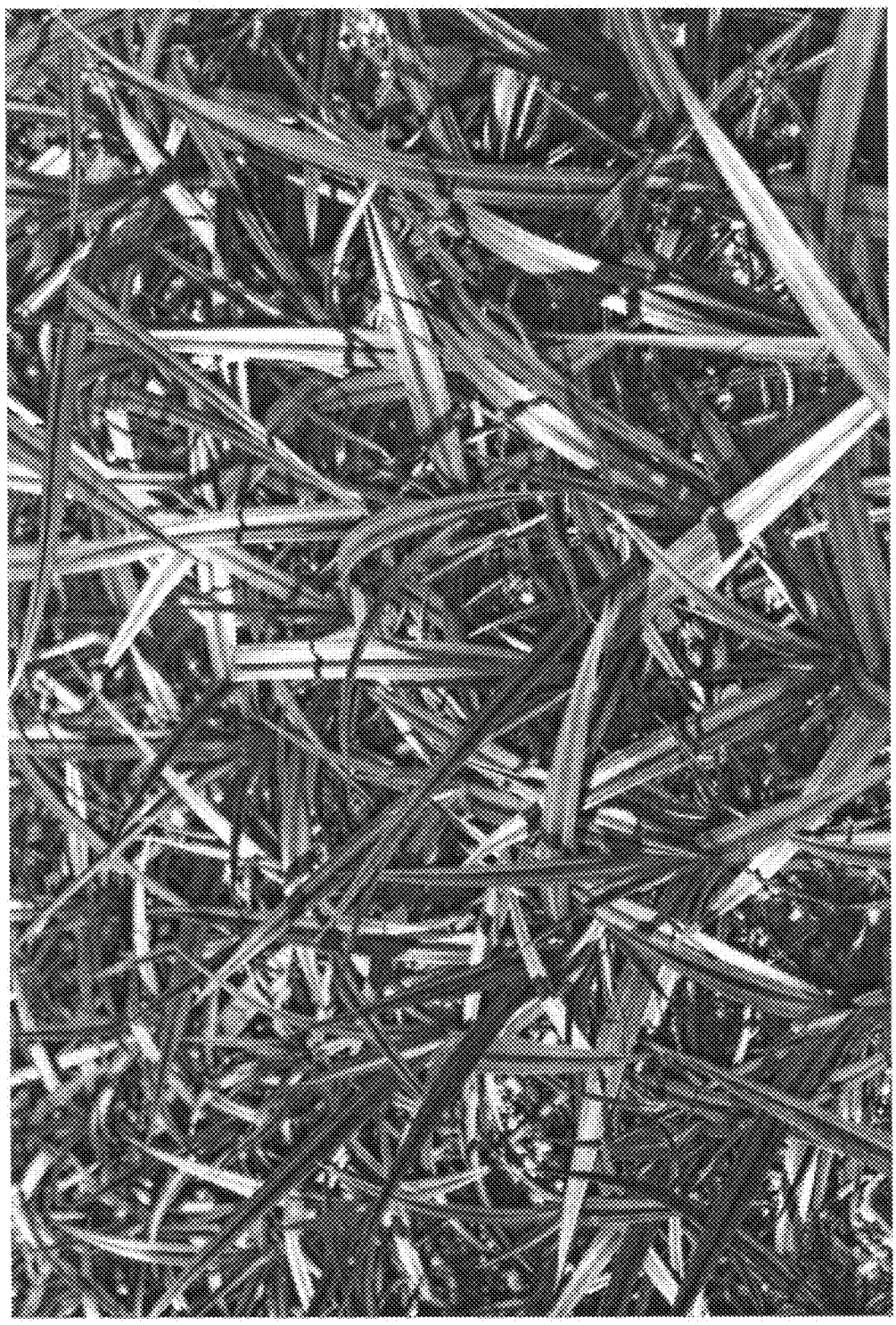
FIG. 1 shows a close up of the foliage.
Figure 2:
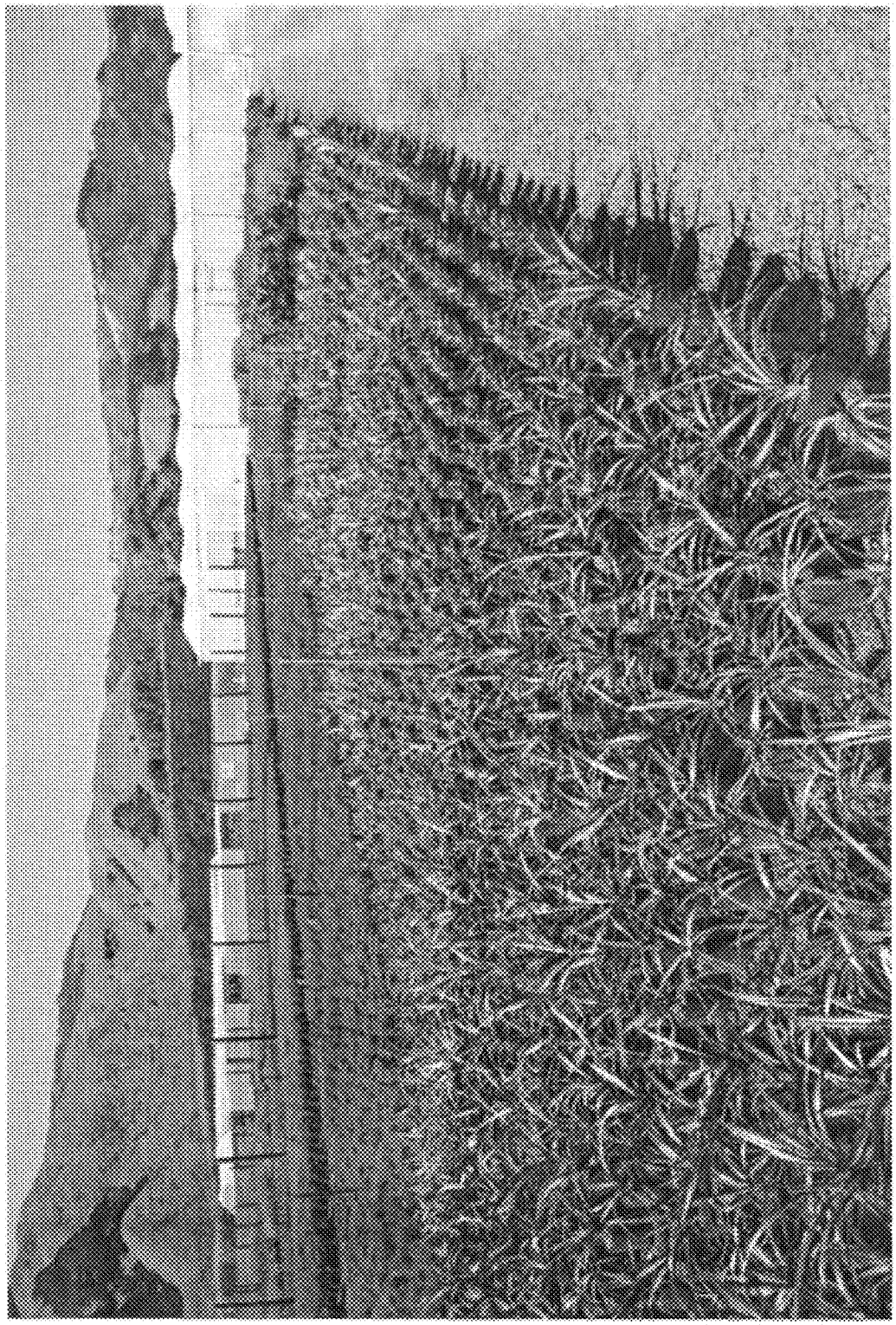
FIG. 2 shows a field of 'AstJe101' grown in 2.5 liter nursery containers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'AstJe101' plants grown outdoors in Te Horo, New Zealand The growing temperature ranged from 15° C. to 35° C. during the day and approximately 10° C. to 25° C. at night. The plants were not grown with any kind of shade protection and subject to outdoor, high light conditions. Measurements and numerical values represent averages of typical plant types. No growth retardants were used.

Botanical classification: *Astelia chathamica* cultivar 'AstJe101'.

PROPAGATION

Time to initiate roots: About 5–10 days at approximately 23° C. from unrooted divisions.
Root description: robust white roots.
Propagation method: Vegetative divisions or tissue culture.

PLANT

Growth habit: Stiff, outwardly arching.
Age of plant described: Approximately 6 months.
Container size: 2.5 liter pot.
Height: Approximately 35 cm to top of highest leaf.
Plant spread: Approximately 25–35 cm.
Growth rate: Rapid early growth rate; from a 5 cm rooted young plant to a 25 cm plant in a 2.5 liter pot takes 3–4 months in peak growing conditions. After reaching approximately 25 cm, growth slows to a moderate rate.
Branching characteristics: Non-branching, forms basal clumps.

FOLIAGE

Leaf:
*Arrangement.*—Non-whorled, basal clumps.
*Average length.*—Approx. 50 cm.
*Average width.*—Approx. 30–50 mm.
*Shape of blade.*—Elliptic.
*Apex.*—Narrowly acute.
*Base.*—Rounded.
*Margin.*—Entire.
*Texture of top surface.*—Tough leathery with noticeable ribs either side of the midrib.
*Texture of bottom surface.*—Tough leathery.
*Quantity of leaves per plant.*—Depends on age of plant, a year 2 year old plant would typically have approximately 50 leaves.
*Color.*—Young foliage upper side: Near RHS Greyed-Brown 200B. Young foliage under side: Near RHS Yellow-Green 148D. Mature foliage upper side: Near RHS Greyed-Purple 187A. Mature foliage under side: Near RHS Greyed-Green 191D.
*Venation.*—Type: Linear. Venation color upper side: Near RHS Greyed-Orange 176A. Venation color under side: Near RHS Greyed-Green 191D.

FLOWER

Natural flowering season: *Astelia chathamica* typically flowers late spring. *Astelia* 'AstJe101' has not yet been observed flowering.

OTHER CHARACTERISTICS

Seeds and fruits: Not observed to date.
Disease/pest resistance: Neither resistance nor susceptibility to pathogens and pests common to *Astelia* have been observed.
Temperature tolerance: Tolerates temperatures from approximately −10° C. to 40° C.

What is claimed is:

1. A new and distinct cultivar of *Astelia chathamica* plant named 'AstJe101' as herein illustrated and described.

* * * * *